(12) United States Patent  
Bui et al.

(10) Patent No.: US 6,629,981 B2
(45) Date of Patent: Oct. 7, 2003

(54) STENT DELIVERY SYSTEM

(75) Inventors: Dennis M. Bui, Orange, CA (US); Sanford D. Damasco, Irvine, CA (US)

(73) Assignee: Endocare, Inc., Irvine, CA (US)

( * ) Notice: Subject to any disclaimer, the term of this patent is extended or adjusted under 35 U.S.C. 154(b) by 0 days.

(21) Appl. No.: 09/816,508

(22) Filed: Mar. 23, 2001

(65) Prior Publication Data

US 2002/0007206 A1 Jan. 17, 2002

Related U.S. Application Data

(63) Continuation-in-part of application No. 09/612,405, filed on Jul. 6, 2000, now Pat. No. 6,413,269.

(51) Int. Cl.[7] .............................................. A61M 29/00
(52) U.S. Cl. ...................................... 606/108; 606/191
(58) Field of Search ................................. 606/108, 191, 606/198, 195, 192, 193, 194, 196, 200; 623/1.11–1.22

(56) References Cited

U.S. PATENT DOCUMENTS

| 4,170,990 A | 10/1979 | Baumgart et al. ............. 128/92 |
| 4,503,569 A | 3/1985 | Dotter ............................. 3/1.4 |
| 4,512,338 A | 4/1985 | Balko et al. .................... 128/1 |
| 4,553,545 A | 11/1985 | Maass et al. ................ 128/341 |
| 4,733,665 A | 3/1988 | Palmaz ........................ 128/343 |
| 4,762,128 A | 8/1988 | Rosenbluth ................. 128/343 |
| 4,795,458 A | 1/1989 | Regan ............................. 623/1 |
| 4,913,141 A | 4/1990 | Hillstead ..................... 606/108 |
| 4,969,890 A | 11/1990 | Sugita et al. ................ 606/192 |
| 5,002,558 A | 3/1991 | Klein et al. ................. 606/192 |
| 5,019,085 A | 5/1991 | Hillstead ..................... 606/108 |
| 5,037,427 A | 8/1991 | Harada et al. ............... 606/108 |
| 5,078,736 A | 1/1992 | Behl ............................... 623/1 |
| 5,147,370 A | 9/1992 | McNamara et al. ......... 606/108 |
| 5,160,341 A | 11/1992 | Brenneman et al. ........ 606/198 |
| 5,178,618 A | 1/1993 | Kandarpa ..................... 606/28 |
| 5,197,978 A | 3/1993 | Hess ............................... 623/1 |
| 5,224,953 A | 7/1993 | Morgentaler ................ 606/192 |
| 5,246,445 A | 9/1993 | Yachia et al. ................ 606/108 |
| 5,306,294 A | 4/1994 | Winston et al. ................ 623/1 |
| 5,466,242 A | 11/1995 | Mori ........................... 606/198 |
| 5,571,135 A | 11/1996 | Fraser et al. ................ 606/198 |
| 5,772,668 A | 6/1998 | Summers et al. |
| 5,776,141 A | 7/1998 | Klein et al. ................. 606/108 |
| 5,776,142 A | 7/1998 | Gunderson .................. 606/108 |
| 5,797,952 A | 8/1998 | Klein .......................... 606/198 |
| 5,816,258 A | 10/1998 | Jervis ......................... 128/898 |
| 5,830,179 A | 11/1998 | Mikus et al. .................. 604/49 |
| 6,033,413 A | 3/2000 | Mikus et al. ................ 606/108 |
| 6,093,194 A * | 7/2000 | Mikus et al. |
| 6,302,898 B1 * | 10/2001 | Edwards et al. |
| 6,416,529 B1 * | 7/2002 | Holman et al. |

FOREIGN PATENT DOCUMENTS

| DK | WO 93/13824 | 7/1993 |
| EP | 0626153 A1 | 11/1994 |
| EP | 0666065 A1 | 8/1995 |

* cited by examiner

*Primary Examiner*—Ismael Izaguirre
(74) *Attorney, Agent, or Firm*—Lawrence N. Ginsberg

(57) ABSTRACT

A stent delivery catheter is disclosed. The catheter includes an inner catheter tube and an outer catheter tube which are rotatable relative to each other. The inner catheter and outer catheter include releasable attachment structures to releasably engage the ends of the stent. A proximal hand piece includes controls for enlarging and deploying the stent in a body lumen.

40 Claims, 11 Drawing Sheets

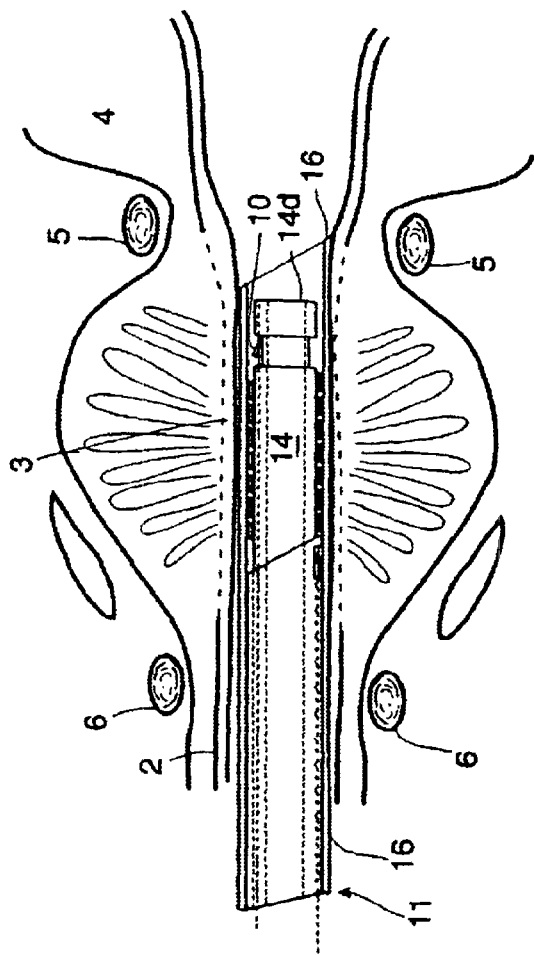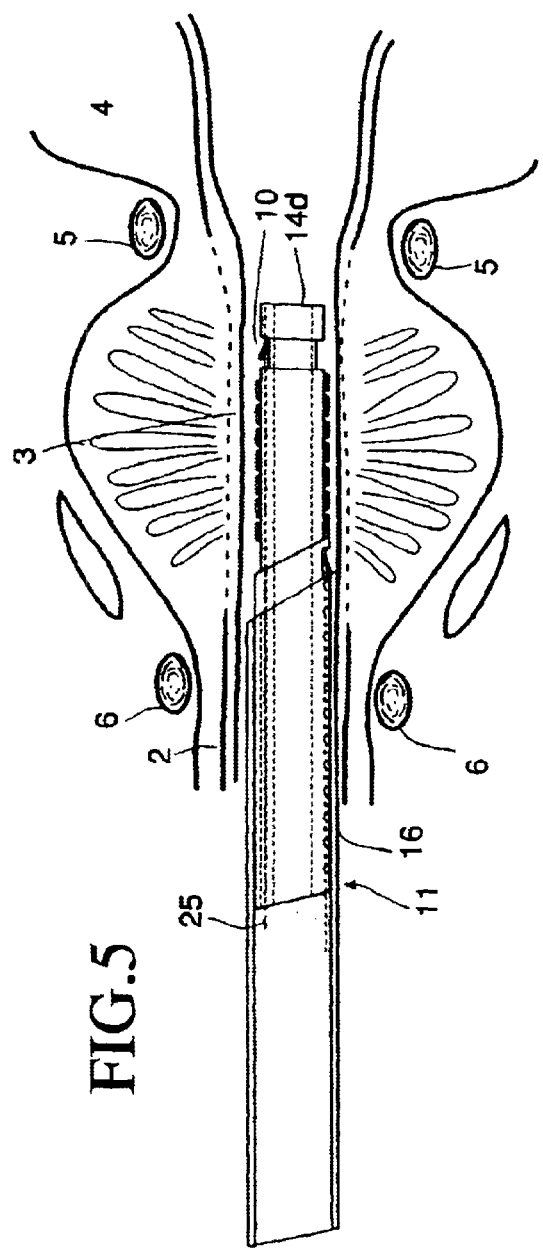

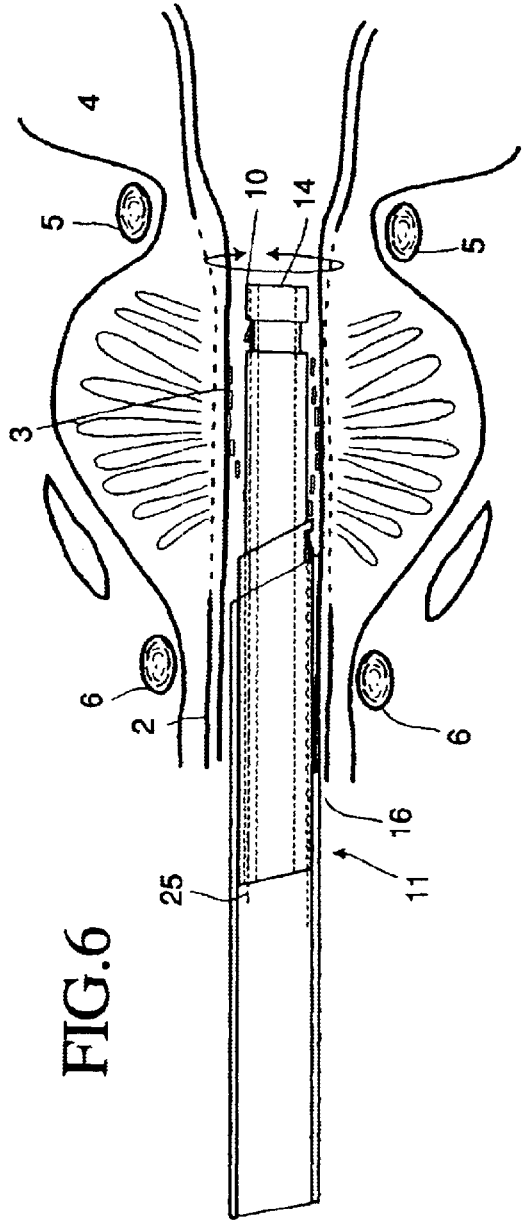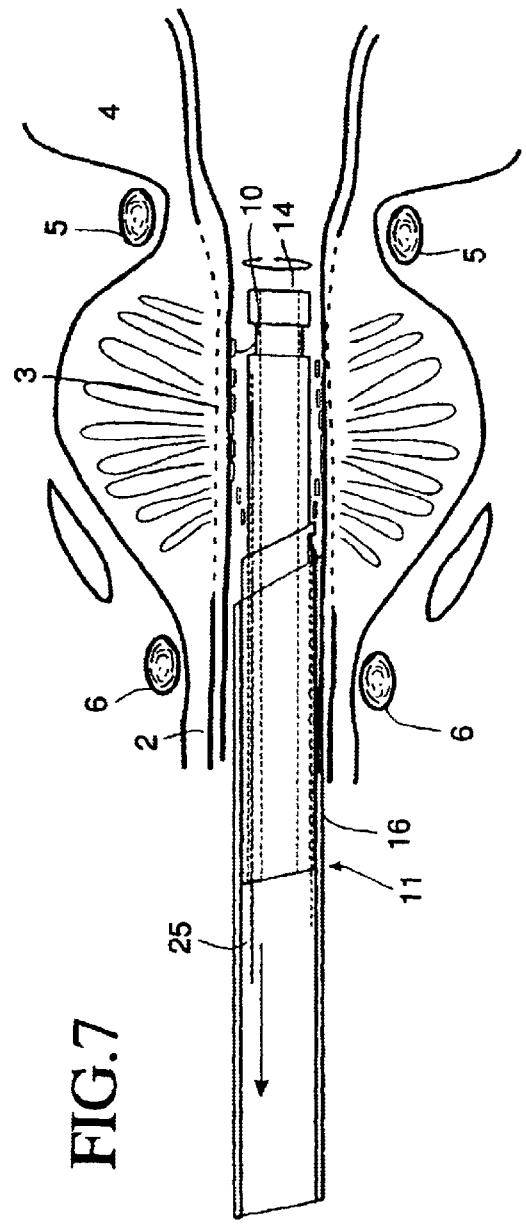

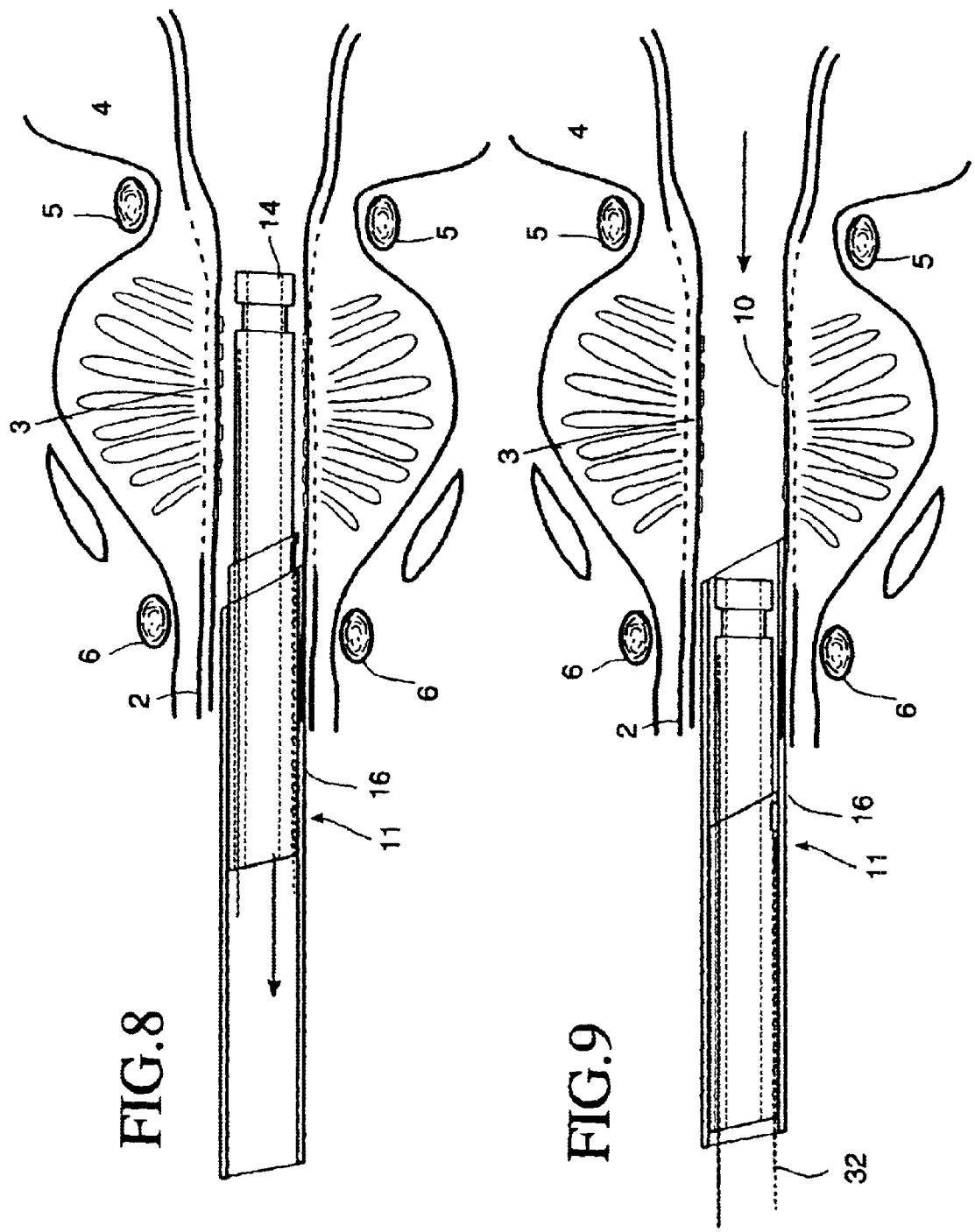

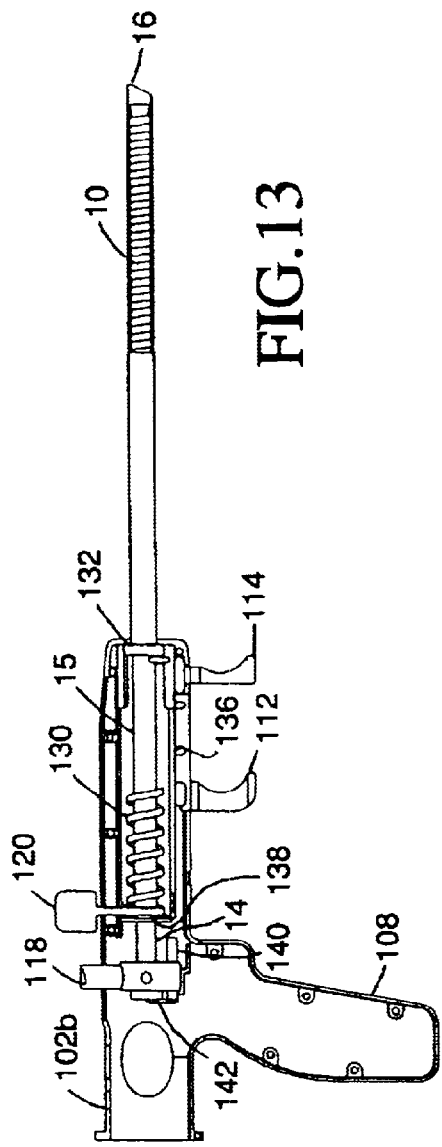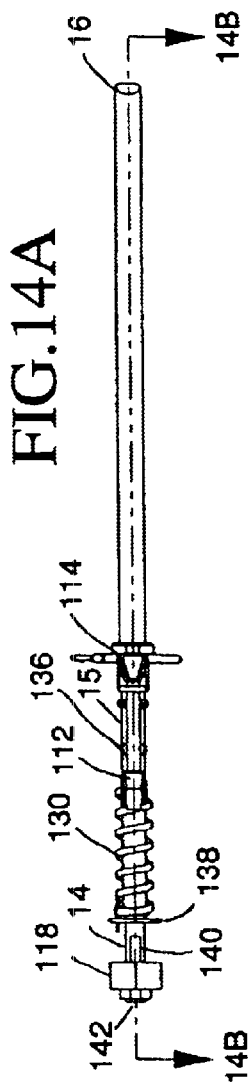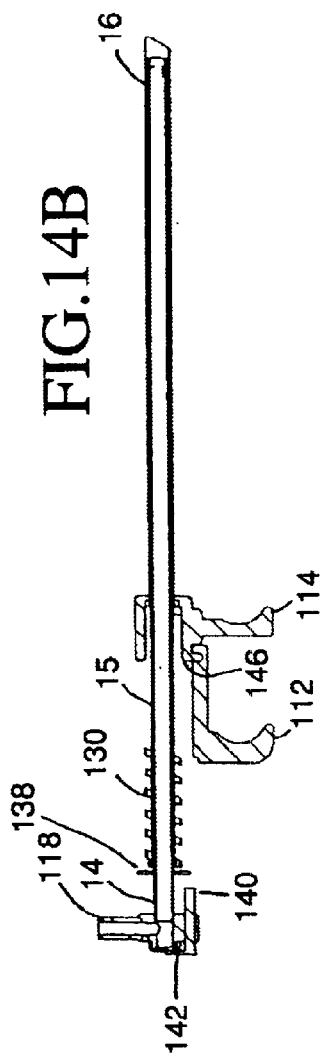

STENT DELIVERY SYSTEM

CROSS-REFERENCE TO RELATED APPLICATION

This application is a continuation-in-part of U.S. patent application Ser. No. 09/612,405, filed Jul. 6, 2000 now U.S. Pat. No. 6,413,269, the entirety of which is hereby incorporated by reference.

BACKGROUND OF THE INVENTION

1. Field of the Invention

This invention relates to stents, urology, and treatments for benign prostate hypertrophy or prostate cancer, as well as methods for correction of vessel occlusions.

2. Description of the Related Art

Prostate enlargement, also known as benign prostate hyperplasia or benign prostate hypertrophy, is a common affliction among older men. The condition involves swelling of the prostate. The prostate surrounds the urethra, or urinary tract, and swelling of the prostate prevents passage of urine from the bladder. Benign prostate hyperplasia is uncomfortable because it makes urination difficult or impossible. The condition is also dangerous because it can lead to infection of the bladder and kidneys, and severe cases may lead to death. Prostate cancer is also a common affliction among older men, and may lead to many of the same symptoms as benign prostate enlargement. Prostate cancer is more dangerous in that it may spread to other organs and is often fatal. Early treatment can reduce the risks of death due to prostate cancer.

Both prostate enlargement and prostate cancer can be treated with heat treatments such as hyperthermia or thermotherapy. As described in U.S. Pat. No. 5,830,179, the entirety of which is hereby incorporated by reference, a stent serves the dual purpose of acting as a heat source for the thermotherapy procedures, as well as acting to hold the urethra open after therapy to prevent blockage due to swelling and prostate tissue sloughing. A stent may be implanted as an interim solution to hold open the urethra while the patient awaits more aggressive surgery or treatment.

A stent may be implanted after hypothermia or cryosurgery to keep the urethra open while enlargement subsides. Finally, a stent may be implanted as a primary treatment. When the stent is implanted for any of these reasons, it is usually better to leave the bladder neck sphincter and the external sphincter unblocked by the stent. These sphincters control the flow of urine through the urethra, and if the stent is placed within these sphincters they will not be able to close. This would leave the patient incontinent. To ensure the proper positioning of the stent, the devices below provide several benefits including controlled release of the stent, tentative initial opening of the stent, and visualization of the bladder and prostatic urethra during placement.

McNamara, et al., *Nitinol Stent For Hollow Body Conduits,* U.S. Pat. No. 5,147,370 (Sep. 15, 1992), the entirety of which is hereby incorporated by reference, describes a catheter delivery system which uses a single pullwire to retain and release a stent wrapped on the distal end of a catheter. The stent must be provided with "retaining means" in the form of pigtails or hooks on the stent ends capable of engaging a pullwire. The catheter must have two holes communicating into a lumen within the catheter, and the stent ends must enter the lumen through the holes. The pullwire is in the lumen, and engages the stent ends which enter the lumen. After release into the lumen, the retaining means are left to hang in the body lumen. This could lead to thrombus formation in blood vessels and undesirable deposition in urethral stents unless addition precautions are taken to avoid the complications. While materials may be developed in which the stent retaining pigtail structures are not set into the form of the stent, common stent alloys such as elgiloy, nitinol and stainless steel will take a set in the form of pigtails if deformed as suggested by McNamara.

Hillstead, *Apparatus And Method For Placement Of A Stent Within A Subject Vessel,* U.S. Pat. No. 4,913,141 (Apr. 3, 1990), the entirety of which is hereby incorporated by reference, discloses a stent delivery device which uses a pullwire running through the central lumen of the catheter and exiting the catheter to run over the stent ends. The stent is deployed by pulling the pullwire proximally, requiring the pullwire to course over intimal and endothelial surfaces of the body lumen to be treated. This could lead to damage of lumenal surfaces and attendant healing responses which are undesirable. Neither McNamara nor Hillstead provide a mechanism which permits retention and release of the stent with a mechanism which remains in the annular space of the stent, and do not present radially extending features such as the radially outwardly protruding pullwires or radially inwardly protruding pigtails.

SUMMARY OF THE INVENTION

The stent delivery systems described below permit placement of stents in the urethra and other body vessels. The devices are intended to deploy a shape memory stent or other resilient stent into the prostatic urethra under direct vision. The surgeons who use the stent delivery systems can easily place the stent within the prostatic urethra and make sure that the stent does not block the bladder neck sphincter.

In one embodiment, the stent is retained on the catheter with one or more retaining wires or rods which engage the stent ends. The catheter is comprised of two coaxial tubes, one inside the other, and the distal end of the stent is secured to the inner tube while the proximal end of the stent is secured to the outer tube. When both ends of the stent are secured to their respective tubes, the tubes may be rotated relative to each other to open the stent or tighten the stent. The stent may be released from the catheter by pulling the pullwires proximally out of engagement with the stent ends. The pullwire which retains the distal end of the stent may be released first, and the location of the distal end of the stent is observed. Once the distal end of the stent is located properly, the proximal end of the stent may be released from the catheter by pulling the pullwire which retains the proximal end of the stent out of engagement with the proximal end of the stent.

In another embodiment, a stent delivery device includes an inner tube and an outer tube. The inner tube has a distal end releasably connectable to the first end of the stent. The outer tube is rotatably slidable over the inner tube and has a distal end releasably connectable to the second end of the stent. In one embodiment, a sheath is provided which is slideable over the outer tube. A trigger may also be provided which is operably connected to the sheath for moving the sheath along the outer tube. In another embodiment, a belt is operably connected to the outer tube for rotating the outer tube relative to the inner tube. The stent may be releasably connectable to the first and second ends of the stent using at least one pullwire.

In accordance with a further aspect of the present invention, there is provided a stent deployment device. The device comprises a tubular body, having a proximal end and a distal end, the tubular body comprising a first and a second stent support. A hand piece is provided on the proximal end of the tubular body. A first control is provided on the hand piece, for manipulating the first stent support, and a second control is provided on the hand piece for manipulating the second stent support.

In one embodiment, the first stent support comprises an outer tubular sleeve for surrounding the stent. The first control comprises a control for proximally retracting the first stent support, to expose at least a portion of the stent. The first control may comprise a slider switch or lever, such as a trigger.

The second stent support may comprise a tubular body, which is releasably connected to at least a first end of the stent. The second control may comprise a control for rotating the second stent support. In one embodiment, the second control comprises a belt which is wrapped around the second stent support. Lateral retraction of the belt causes a commensurate rotation of the second stent support.

Preferably, the first and second stent supports are concentric tubes, and the stent deployment device further comprises a third stent support, comprising a third tube such that the third stent support forms an inner tube which carries the stent and is releasably connected to a distal end of the stent. The second stent support comprises an intermediate tube, concentrically carried by the inner tube, and releasably secured to a proximal end of the stent. The first stent support comprises an outer tube, concentrically carried by the intermediate tube, for covering the stent during transluminal positioning of the stent deployment device.

Preferably, the third stent support comprises an inside diameter which is greater than the outside diameter of an optical visualization device such as an endoscope which is releasably mounted to the stent deployment device, thereby forming an annular lumen extending distally through the tubular body. An infusion port may be provided on the hand piece, for communication with the annular lumen, to permit infusion of fluid media through the tubular body and out of the distal end thereof.

Further features and advantages of the present invention will become apparent from the detailed description of preferred embodiments which follows, when considered together with the attached drawings and claims.

BRIEF DESCRIPTION OF THE DRAWINGS

FIG. 4 illustrates initial insertion of a stent delivery system into the prostatic urethra.

FIG. 5 further illustrates the procedure of installing a stent in the prostatic urethra, following retraction of an outer introduction sheath.

FIG. 6 further illustrates the procedure of installing a stent in the prostatic urethra, following partial deployment of the stent.

FIG. 7 further illustrates the procedure of installing a stent in the prostatic urethra, following release of the distal end of the stent.

FIG. 8 further illustrates the procedure of installing a stent in the prostatic urethra, following release of the proximal end of the stent.

FIG. 9 further illustrates the procedure of installing the stent in the prostatic urethra, during proximal retraction of the deployment device.

FIG. 13 is a partial cross-sectional view illustrating the interior components of the stent delivery device of FIG. 10.

FIG. 14A is an underside view of the interior components of the stent delivery device of FIG. 10.

FIG. 14B is a cross-sectional view of the interior components of FIG. 14A.

DETAILED DESCRIPTION OF THE PREFERRED EMBODIMENTS

Figure 1:
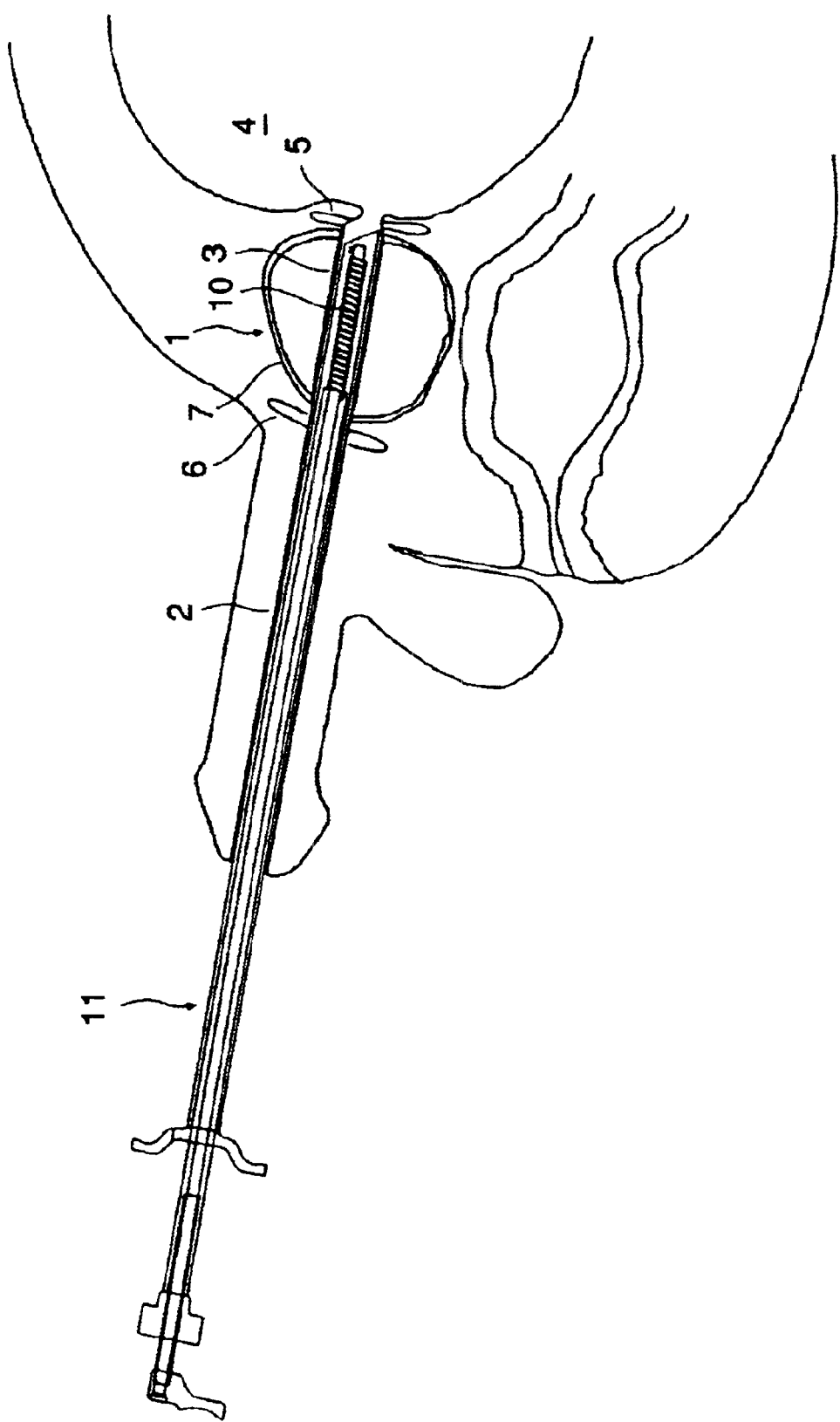
FIG. 1 illustrates a use of a stent delivery system in the treatment of prostate disease in accordance with one embodiment of the present invention.

FIG. 1 shows an overview of a procedure for which a stent and stent delivery system may be used in the treatment of benign prostate hyperplasia or prostate cancer in accordance with one preferred embodiment of the present invention. The details of the local anatomy shown in this figure include the prostate gland 1, the urethra 2 and the prostatic urethra 3. The urethra is the channel which conducts urine from the bladder 4 to the penis for discharge from the body. The prostatic urethra is a continuation of the urethra, and it joins the prostate gland to the urethra. The bladder neck sphincter 5 controls flow of urine from the bladder 4, and the external sphincter 6 controls flow of urine or ejaculate from the bladder 4 or prostate 1. The prostate capsule 7 surrounds the prostate gland. The prostate gland consists of various tissues, including glandular tissue (which produces ejaculate), muscular cells, and epithelial cells. The inside diameter of urethra 2 is typically about 2 centimeters, and the prostatic urethra varies in length from about 15 to 75 mm.

The condition of benign prostate hyperplasia causes the prostate to swell and close off the prostatic urethra. The prostatic urethra 3 is squeezed shut by the swollen prostate, and has an occluded region which must be treated. The stent 10 mounted on the distal portion of delivery catheter 11 is shown ready for placement in the occluded portion of the prostatic urethra. The stent is positioned and released within the prostate through the operation of the delivery catheter as described below. The delivery catheter illustrated in FIG. 1 is rigid, so that the urethra has conformed to the straight configuration of the delivery catheter.

The stent is preferably made of a nitinol alloy with a martensite transition temperature slightly below body temperature, in the range of about 30–35° C. (about 86–95° F.) (this range is conveniently established or maintained with cold saline flow through the catheter or a catheter sheath). Thus, when the stent is cooled below body temperature by cold saline flow, it will enter the soft and pliable martensite state of the alloy. The chosen alloy has a wide hysteresis, so that it remains in the soft and pliable martensite state for a temperature range distinctly above the temperature at which it converts to martensite upon cooling. The transition temperature for the change to the austenitic state upon heating may be varied. It may be just below body temperature, so that warming to body temperature is sufficient to induce reversion to the memorized large diameter configuration. If heating sources are used, the transition temperature may be slightly above body temperature, in the range of about 38–60° C. (about 100–140° F.) or even higher, depending on the heating source used. When hot saline solution is used, about 38–60° C. is convenient because that temperature range can be easily achieved by flushing hot saline through the catheter into the vicinity of the stent (100° C. is the equivalent to 212° F., the boiling point of water, so it can be appreciated that the temperature range of about 38–60° C. is easily achieved in the operating room). Other stent materials may be used in conjunction with the delivery system such as stainless steel, plastics, elgiloy and other resiliently deformable materials. Even plastically deformable stent materials such as tantalum may be used.

Figure 2:
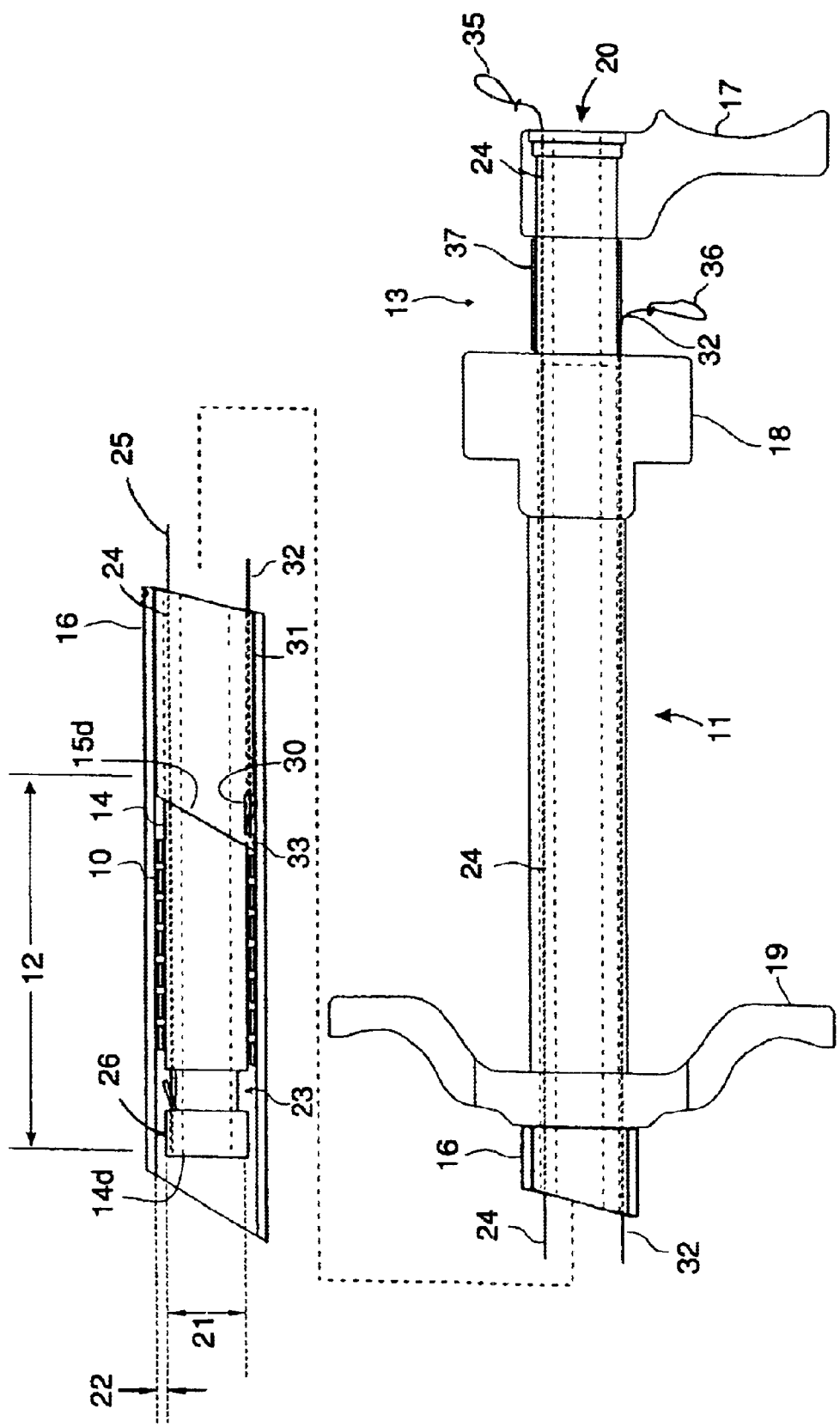
FIG. 2 is a cross section of the stent delivery system of FIG. 1.

FIG. 2 illustrates one stent delivery system. The stent 10 is mounted on the delivery catheter 11 in the distal portion referred to as the stent loading zone 12. The catheter is controlled and the stent is released through operation of the operating mechanism in the proximal end 13 of the delivery catheter. The delivery catheter is comprised of an inner catheter 14 and an outer catheter tube 15 disposed coaxially over the inner catheter, and a sheath 16 coaxially disposed over both the inner catheter and the outer catheter tube. The outer catheter tube and inner catheter are rotatable relative to each other about the longitudinal axis of the catheter, and may be rotated using the proximal handle 17 mounted on the proximal end of the inner catheter and proximal handle 18 mounted on the proximal handle of the outer catheter tube. The inner catheter and outer catheter tube may also slide longitudinally relative to one another. The sheath 16 may also slide relative to the inner catheter and outer catheter tube, and may be operated with the proximal sheath handle 19. The sheath 16 may be rotatable as in the embodiment shown, where no structure inhibits rotation. Alternatively, the sheath may be rotationally fixed relative to either the inner catheter or outer catheter tube, with, or example, a longitudinally oriented tongue and groove structure or spline and keyway structure mating the sheath to the outer catheter tube.

The inner catheter may be a substantially solid cylinder or it may be a hollow tube, in which case it may accommodate an endoscope for viewing the prostatic urethra and stent location before the stent is released. The endoscope lumen 20 shown in FIG. 2 has an diameter approximating common endoscopes. Alternatively, the diameter of lumen 20 may exceed the outside diameter of the scope, to leave an annular channel surrounding the scope for the introduction of saline or other fluid such as to assist in visualization through the scope. The inner catheter, outer catheter and sheath may be made of a transparent plastic or glass so that anatomical landmarks of the prostatic urethra may be seen through the catheter. Medical grade materials, such as stainless steel, may also be used. The components may be rigid, and comprised of stiff transparent plastic such as polyethylene terephthalate (PET) or polycarbonate which facilitates placement in the urethra, but may be made of a flexible transparent or opaque material for placement in other areas of the body where flexibility will facilitate placement. The overall length of the delivery system is generally within the range of about 25 cm to about 50 cm, and in one embodiment, may be about 35 cm (about 14 inches) when constructed for placement of the stent in the urethra.

The outside diameter of the inner catheter diameter 21 at the loading zone 12 is chosen such that, when the stent is wrapped tightly about the distal tip, the overall diameter of the inner catheter and stent is approximately the same as the outer diameter of the outer catheter tube 15. In other words, the inner tube 14 has an outer diameter equal to the outer catheter tube minus twice the stent thickness 22, and the combined inner catheter and stent are isodiametric with the outer catheter tube. The inner diameter of the outer catheter tube is chosen to provide snug but slidable and rotatable fit over the inner catheter, at least near the loading zone. The inner diameter of catheter sheath 16 is chosen to provide snug but slidable and rotatable fit over the outer catheter and stent.

Near the distal tip 14d of the inner catheter 14, an annular recess 23 or notch is formed in the outer wall. The recess or notch does not extend entirely through the catheter wall. In the embodiment shown, the annular recess extends to a depth equal to or greater than the stent thickness. Cut-outs or holes extending entirely through the catheter wall may be used in lieu of the recess or notch. The inner catheter has a side lumen 24 which passes from the distal end of the catheter, at least from the annular recess 23 proximally to the proximal end of the delivery system. The side lumen 24 opens into the annular recess 23. A first pullwire 25, disposed within a side lumen of the inner catheter, extends from the proximal end of the delivery system to the annular recess. The pullwire extends further distally to engage the stent, and, optionally, into the distal extension 26 of the pullwire lumen beyond the annular recess. The pullwire engages a hole 27 or hook in the distal end of the stent (visible in FIG. 3), and thereby retains the distal end of the stent 10 to the distal end 14d inner catheter. The pullwire is preferably sufficiently stiff and rigid to be both pulled and pushed within the pullwire lumen, so that the pullwire may be engaged within the recess to re-engage the stent with the delivery system in order to remove the stent or adjust its position after placement.

Near the distal tip 15d of the outer catheter 15, an annular recess 30 or notch is formed in the outer wall. As with the inner catheter recess, the recess or notch does not extend entirely through the catheter wall. In the embodiment shown, the annular recess extends to a depth equal to or greater than the stent thickness. Cut-out or holes extending entirely through the catheter wall may be used in lieu of the recess or notch. The outer catheter has a side lumen 31 which passes from the distal end of the catheter, at least from the annular recess proximally to the proximal end of the delivery system. The side lumen 31 opens into the annular recess 30. A second pullwire 32, disposed within the side lumen 31 of the outer catheter 15 extends from the proximal end of the delivery system to the annular recess 30. The pullwire 32 extends further distally to engage the stent, and, optionally, into the distal extension 33 of the pullwire lumen beyond the annular recess. The second pullwire 32 engages a hole 34 or hook in the proximal end of the stent (visible in FIG. 3), and thereby retains the proximal end of the stent to the distal end 15d of the outer catheter tube. Again, the pullwire is preferably sufficiently stiff and rigid to be both pulled and pushed within the pullwire lumen, so that the pullwire may be engaged within the recess to engage the stent.

Referring now to the proximal end of the stent delivery catheter, the first and second pullwires exit their respective lumens and terminate in pull rings 35 and 36 which can be used to pull the pullwires proximally. When the pullwires are pulled proximally, the ends of the stent which they hold in the annular recesses are released. Interposed between the inner catheter handle 17 and the outer catheter handle 18 is a collet 37. The collet serves to lock the inner catheter and outer catheters longitudinally in relation to each other until longitudinal movement is desired. When movement is desired, the collet is easily removable, and is provided with a longitudinal slit to permit easy removal by the operator during surgery.

The stent delivery system is assembled by wrapping a helical stent around the distal end of the inner catheter tube 14 and placing the distal end of the stent in the recess of the inner catheter tube and placing the proximal end of the stent in the recess of the outer catheter. The stent is secured on the stent delivery system by passing the first retaining wire longitudinally through the wall of the inner catheter tube to enter the recess of the inner catheter tube and engage the distal end of the stent within the recess, and then passing a second retaining wire longitudinally through the wall of the outer catheter to enter the recess of the outer catheter and engage the proximal end of the stent within the recess. The sheath is then slipped over the entire assembly. If the stent is a nitinol or shape memory alloy or polymer susceptible to superelastic behavior, it is best to assemble the device while maintaining the stent below the superelastic temperature range or the shape recovery transition temperature.

Figure 3:
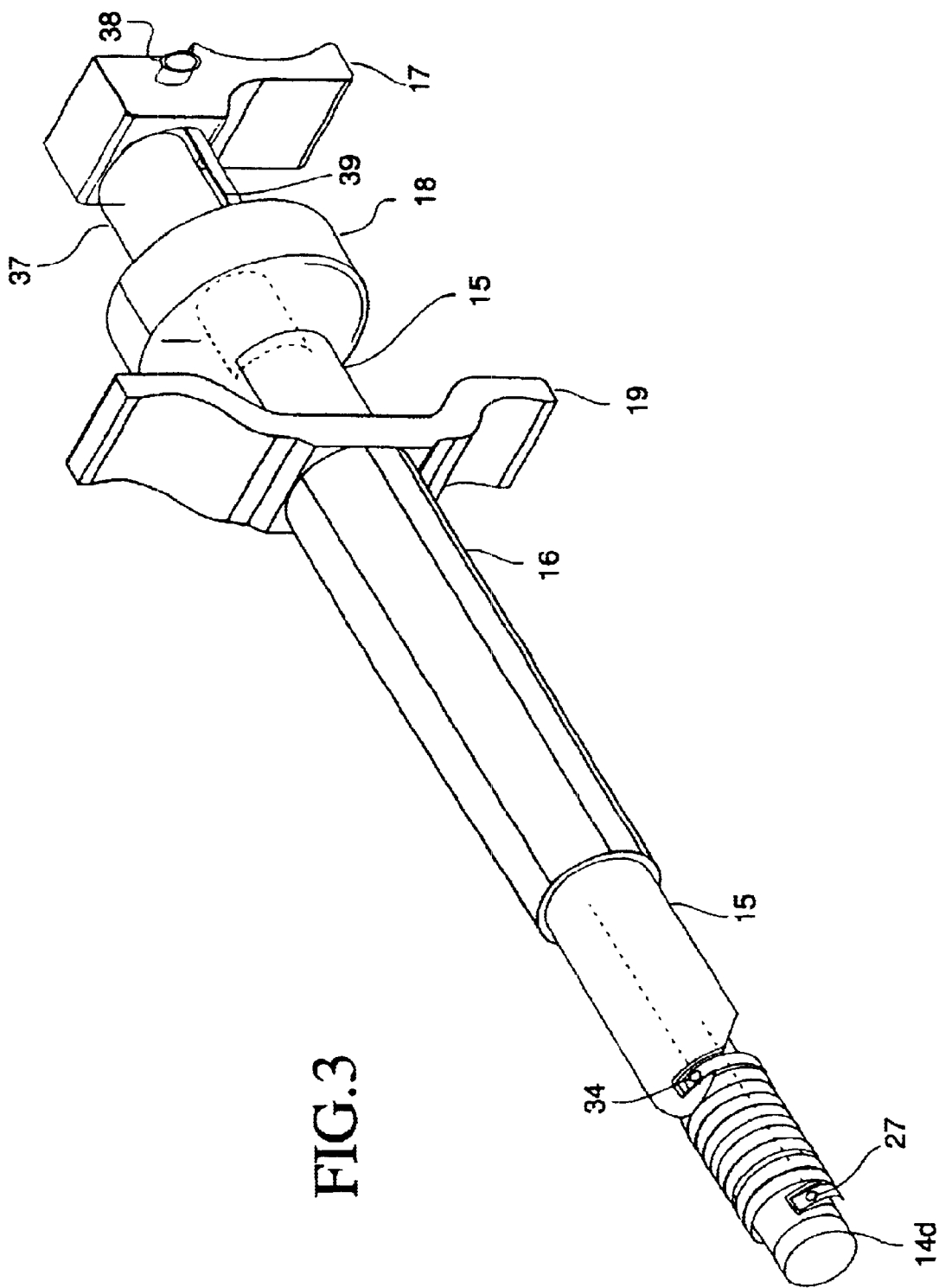
FIG. 3 is a perspective view of the stent delivery system of FIG. 1.

FIG. 3 is a front perspective view of the stent delivery system. In this view, additional features are visible. The proximal handle 17 for the inner catheter tube 14 is fitted with two luer fittings 38 (only one is visible in this view) which permit injection of fluids as required during the procedure. The slit 39 of collet 37 permits easy installation and removal. At the distal end of the delivery catheter, the disposition of the stent distal and proximal end in the recesses 23 and 30 is visible. The pullwires do not need to exit the catheter lumen to engage the stent, and do not pass radially through the catheter wall in order to engage the stent. Additionally, the stent ends to not need to enter the lumen of either the inner catheter or the outer catheter in order to engage with the pullwires, and there is no need for cut-outs in the catheter walls to allow passage of the stent ends into the interior of the catheter. Indeed, the outer catheter lumen is taken up completely by the diameter of the inner catheter, so that the stent ends cannot enter this lumen.

FIGS. 4 through 8 depict placement of the stent. FIG. 4 illustrates initial insertion of the stent delivery system into the prostatic urethra. The surrounding anatomy is shown in a frontal view, and corresponds to the anatomy shown in FIG. 1. The stent has been tightly wound on the stent loading zone of delivery catheter 11, and has a small diameter of about 0.75 to 1 cm (0.25 to 0.40 inches) that fits easily into the urethra 2. When coiled for insertion, the stent is about 4.5 cm (1.75 inches) long. The catheter sheath 16 is provided to cover the stent during placement and provide a smooth outer surface to facilitate placement of the stent. The delivery system is then pushed through the urethra until the stent is located in the prostatic urethra 3, as shown in FIG. 4. An endoscope is placed within the lumen of the inner catheter so that correct initial placement may be verified visually. Preferably, the operator will insert the catheter until the distal end of the sheath is aligned with bladder neck or about 0.25 cm short of the bladder neck. This will locate the stent delivery zone of the catheter between the bladder neck sphincter 5 and the external sphincter 6 inside the prostatic urethra 3.

The next step of the procedure is illustrated in FIG. 5. Having visually confirmed the position of the stent, the operator pulls the sheath 16 proximally until the stent 10 and the distal tip 14d of the inner catheter 14 is exposed. The stent, along with the inner catheter and outer catheter tube, are maintained in position by holding the proximal handles in place while the sheath handle 19 (shown in FIG. 2) is pulled proximally. Next, as illustrated in FIG. 6, the inner catheter 14 is rotated (using the proximal handle 17, shown in FIG. 2) relative to the outer catheter tube 15. This forces the stent to open partially (the proximal and distal ends of the stent are still attached to the delivery system via the pullwires) and partially engage the prostatic urethra 3. The operator may visually confirm the location of the stent and proper opening of the stent through the endoscope. If the stent location is not acceptable, the stent is flushed with cold saline to bring the stent temperature down to the martensite range. This softens the stent, making it pliable and easily re-tightened on the stent loading zone by rotating the inner catheter in the tightening direction. The cold stent is then tightened on the inner catheter by rotating the inner catheter relative to the outer catheter.

When the stent location is acceptable, the distal end of the stent may be released as illustrated in FIG. 7. The pullwire 25 in the inner catheter is pulled proximally and out of engagement with the distal end of the stent. The distal end of the stent is then released to engage the prostatic urethra. Again, the position of the stent may be visually checked through the endoscope, by viewing through the inner catheter wall. If the stent is not properly located, it is preferable to cool it with cold saline to soften, it pull it into the outer sheath and remove it from the body. The procedure can be repeated with a replacement delivery system or the stent can be reloaded on the catheter and re-used where appropriate.

With the stent partially released and properly located, the proximal end of the stent may be released as illustrated in FIG. 8. The operator pulls the pullwire 32 proximally, out of engagement with the proximal end of the stent, and the proximal end of the stent is released to expand into engagement with the prostatic urethra. When fully released, the stent will expand radially up to about 1 cm (0.4 inches) and contract longitudinally (foreshorten) to about 2.5 centimeters (one inch) in length: The actual diameter and length of the stent within the prostatic urethra will vary according to the physical condition of the prostatic urethra, the physical attributes of the stent, and the manipulation by the operator. After placement of the stent, all components of the delivery system are withdrawn from the urethra, as illustrated in FIG. 9 and the stent insertion procedure is complete.

After placement in a swollen prostate, as depicted in FIG. 9, the stent will be firmly held by the compressive forces of the prostate. The stent may be flushed with hot saline to cause the stent to heat up well above its austenite transition temperature. Of course, if the stent transition temperature is at or below body temperature, it will be sufficient to allow the stent to be heated to the austenite transition temperature by surrounding body temperature without injection of warm saline solution. The stent may be left in the urethra for some time, either as a temporary palliative for prostate ablation or it may remain in place permanently with due care taken to avoid infection.

It will be appreciated that various devices may be suitable for delivering the stent 10, Generally, a stent delivery device will advantageously enable the proximal and distal ends of the stent to be rotated relative to one another, while also providing for releasable attachment of the stent to the device. In the example given above, this is accomplished using inner and outer tubes that are rotatable relative to one another, and pullwires that connect the ends of the stent to the tubes. It will be appreciated, however, that other mechanisms may also be used to accomplish these objectives. For example, the ends of the stent could be held with an adhesive that releases the stent once it contacts a certain type of irrigation fluid or temperature.

In the embodiment described above having an inner catheter 14 and an outer catheter tube 15, a sheath 16 is provided to protect the stent during delivery. It will be appreciated, however, that the stent 16 may not always be necessary. Moreover, a delivery device is contemplated in which the sheath 16 can be moved proximally relative to the outer catheter tube 15 to a fixed location, such that the distal end of the sheath is positioned between the proximal and distal ends of the stent. This enables the stent to be deployed partially while still retaining the stent within the device. Moreover, a device is contemplated in which the rotation of the proximal end of the stent relative to its distal end can be accurately controlled in order to prevent over or under expansion of the stent.

Figure 10:
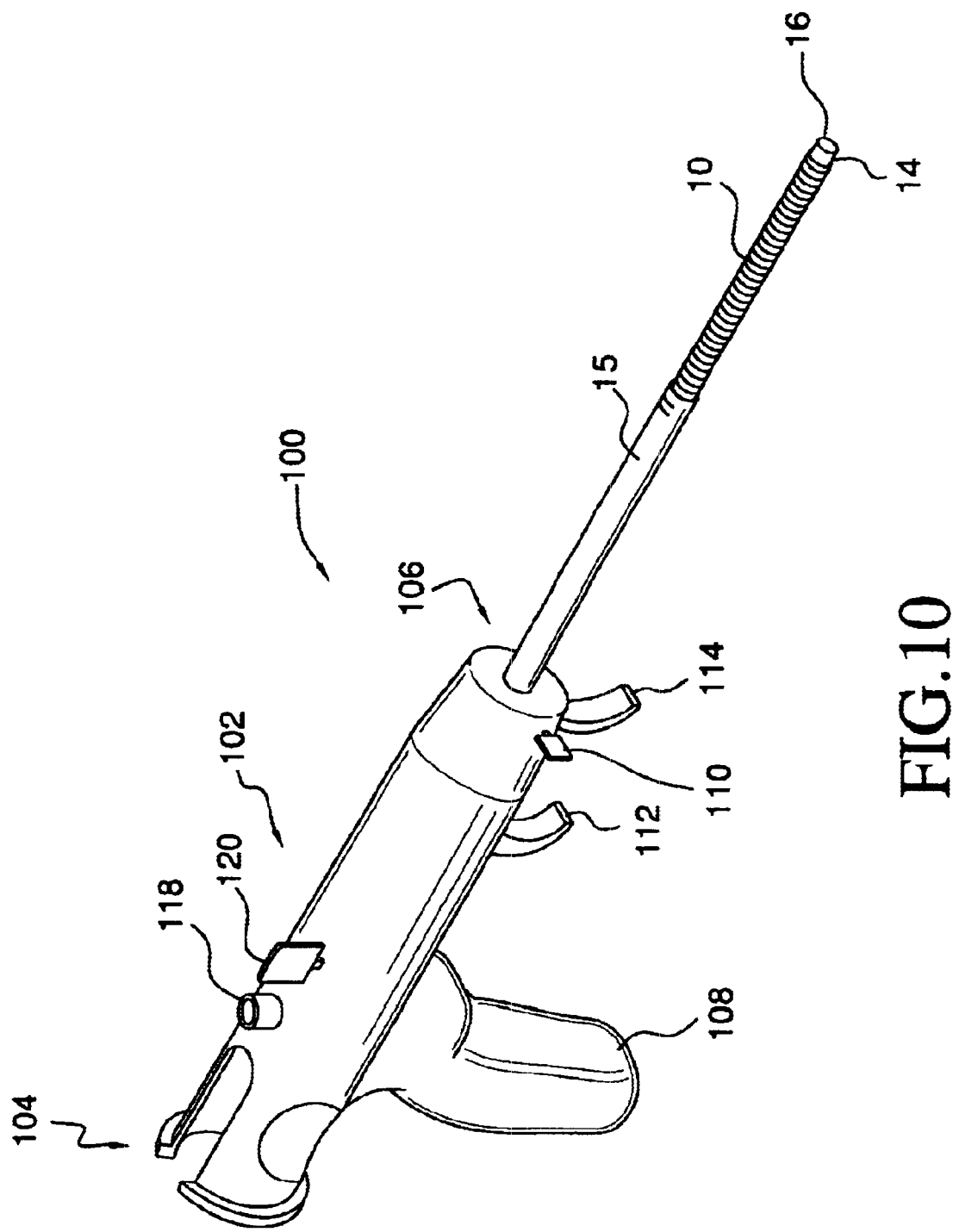
FIG. 10 is a perspective view of a stent delivery device in accordance with another embodiment of the present invention.

These and other features are provided in another example of a stent delivery device shown in FIG. 10. The delivery device 100 in one preferred embodiment includes an inner catheter 14, outer catheter tube 15 and sheath 16 as described above, each of these components being operably connected to a main body 102. The inner catheter 14 and outer catheter tube 15 releasably carry a helical stent 10 in the same manner as described above, i.e., by engaging pullwires 25 and 32 (not shown) which extend into the main body 102.

The main body 102 may include a generally cylindrical housing, extending between a proximal end 104 and a distal end 106, and includes a handle 108 by which an operator can grasp the delivery device 100. The main body further includes a retaining pin 110, described in further detail below, which prevents the sheath or first stent support 16 from moving while the pin is in place. Depending from the underside of the cylindrical body and distal to the handle 108, a control such as a pair of triggers 112 and 114 are provided, which slide within a groove (not shown) in the underside of the main body 102 for moving the sheath 16. An irrigation port 118 as described below extends from the top of the main body 102 and is in fluid communication with the inner lumen of the catheter 14. A rip cord or belt 120 connected to the outer catheter tube 15 also extends from the top of the main body 102 which, when pulled as described below, rotates the outer catheter tube 15 with respect to inner catheter 14 to partially open the stent 10.

Figure 11:
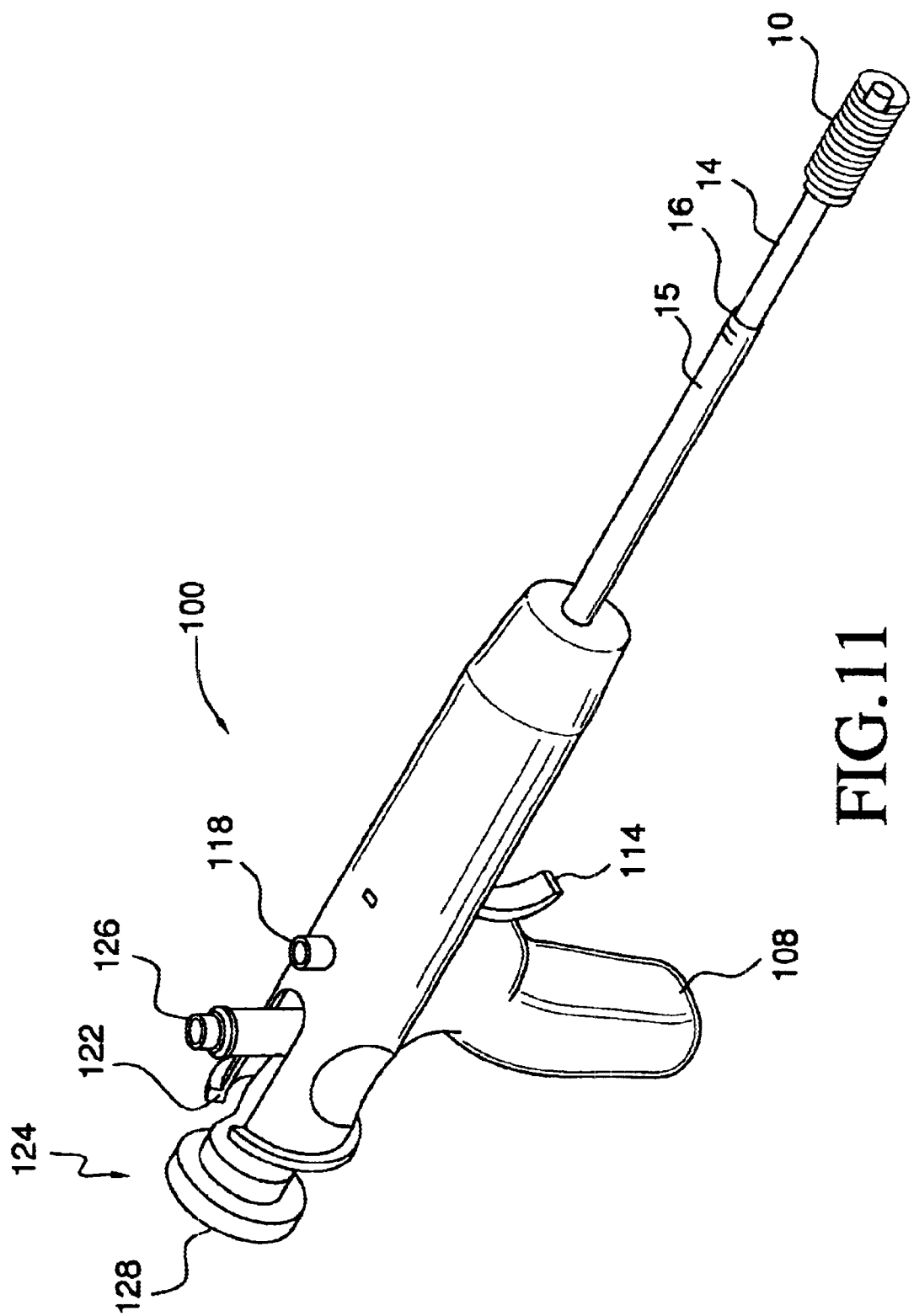
FIG. 11 is a perspective view of the stent delivery device of FIG. 10, showing the stent deployed and showing an endoscope in the proximal end of the device.

FIG. 11 illustrates the stent delivery device after the stent 10 has been deployed. As shown, at the proximal end of the main body 102, and provided within slot 122, an endoscope 124 is locked into place against the main body 102. The endoscope 124 preferably includes a first port 126 for receiving a light source and a second port 128 for visualization. The endoscope 124, when inserted into the main body 102, preferably forms a fluid tight seal therewith, on the proximal side of the irrigation port.

Figure 12:
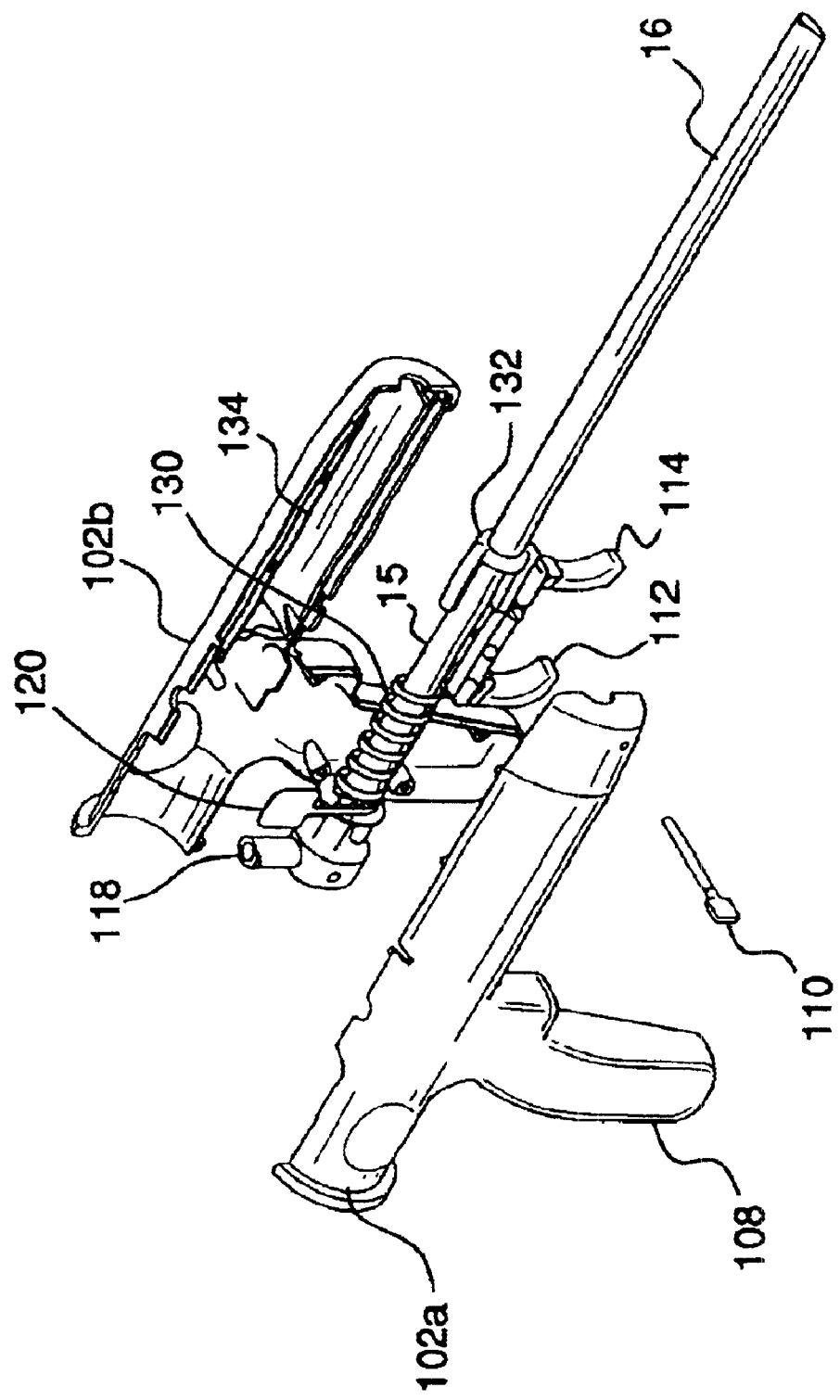
FIG. 12 is an exploded perspective view of the stent delivery device of FIG. 10.

FIGS. 12–14B illustrate more particularly the interior components of the stent delivery device 100. As shown in FIG. 12, the main body 102 may be formed from two halves 102a and 102b which can be secured together by screws, adhesives or other means. The sheath 16 at is proximal end is connected to an annular base 132, which slides along the outside of outer tube 15. To move the annular base 132, and thus to move sheath 16, trigger 114 engages the annular base, as shown in FIG. 14B, to move the sheath proximally. Trigger 114 preferably slides along grooves 134 provided in each of the main body halves 102a and 102b.

As shown in FIG. 14B, a second trigger 112 may be removably connected with trigger 114. When triggers 112 and 114 are in their distalmost position, trigger 112 engages trigger 114 such that they are both moveable together. As discussed above, trigger 114 slides along groove 134 in the body halves 102a and 102b, and also slides along a groove (not shown) on the underside of the main body. The trigger 112 is provided with a pin 136 which has a length which is longer than the width of the groove on the underside of the main body 102. This prevents the trigger 112 from falling out of the main body 112. When the trigger 112 is slid proximally and reaches its proximalmost point (i.e., just distal to the handle 108), the pin 136 becomes aligned with a portion of the groove on the underside of the main body which has an increased width. Upon reaching this point, the trigger 112 can be removed through the groove on the underside of the main body, thereby leaving only trigger 114 in the main body 102.

The movement of the triggers 114 and 112 proximally until the trigger 112 is removed coincides with the sheath 16 moving proximally along the stent 10 such that the distal end of the sheath is located between the proximal and distal ends of the stent. More preferably, the sheath 16 exposes approximately half of the stent secured to the inner and outer tubes. It will be appreciated that other mechanisms for limiting the proximal motion of the sheath 16 along the stent 10 may be provided.

As shown in FIG. 13, the rip cord 120 is connected to a helically wound belt 130 which is connected to the outer tube or second stent support 15. It will be appreciated that the belt can be permanently or removably attached to the outer tube 15. Thus, by pulling on the rip cord 120, the belt 130 rotates the outer tube 15 relative to the inner tube or third stent support 14. With the stent 10 connected to the inner and outer tubes as discussed above, this causes the stent 10 to expand after the sheath 16 has been removed. When the belt 130 is removably attached to the outer tube, pulling of the rip cord causes the belt 130 to disengage from the outer tube.

The belt 130 is preferably provided with a plurality of regularly spaced bumps and grooves, such that as the belt 130 is pulled away from the main body 102, the bumps indicate a fixed interval of rotation of the outer tube 15 relative to the inner catheter 14. Preferably, the length of the belt coincides with the desired amount of rotation of the outer tube 15 relative to the inner tube 14, such that the amount the stent 10 is expanded is accurately controlled.

FIGS. 13, 14A and 14B further illustrate the mechanism for removing the pullwires 25, 32 (shown above in FIG. 2) from the stent 10. Pullwire 32 of outer tube 15 at its proximal end extends through annular disc 138, which is connected to the proximal end of outer tube 15. Pullwire 32 has an enlarged portion at its proximal tip, such that movement of annular disc 138 in a proximal direction causes proximal movement of the pullwire 32. Similarly, pullwire 25 of inner tube 25 extends through a plate 142, and has an enlarged proximal tip such that movement of plate 142 in a proximal direction causes proximal movement of the pullwire 25.

After the trigger 112 and the belt 130 have been removed, the trigger 114 can be moved further proximally toward the disc 138 and plate 142. The trigger 114 has a rear surface 146 that will first contact the plate 138, moving it proximally and causing the pullwire 32 to move proximally out from the proximal end of the stent 10. The rear surface 146 then will cause the annular disc 138 to contact a rod 140 extending through the manifold 118, causing the rod 140 to slide relative to the manifold and move proximally. The proximal end of this rod will contact the plate 142 and move it proximally, and cause the pullwire 25 to release the distal end of the stent 10.

Although the embodiment described above provides for the proximal end of the stent 10 to be released prior to the distal end of the stent, it will be appreciated that the pullwires 25 and 32 could be removed simultaneously, or the pullwire 25 could be removed first at the distal end of the stent prior to removal of the pullwire 32 from the proximal end of the stent.

Figure 15:
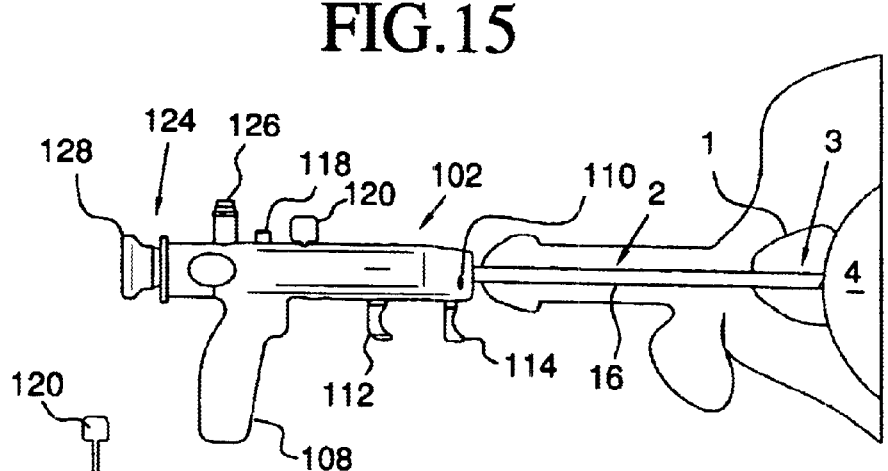
FIGS. 15–17 illustrate the use of the stent delivery device of FIG. 10 in the treatment of prostate disease.
Figure 16:
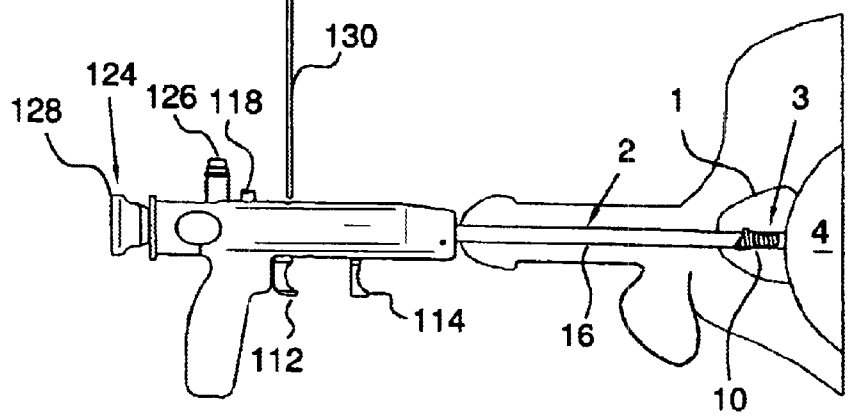
Figure 17:
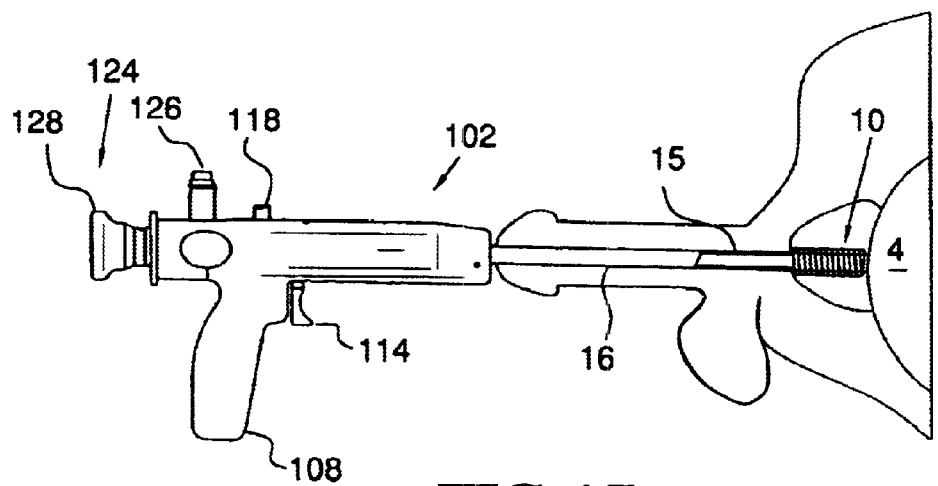

FIGS. 15–17 illustrate the operation of the device 100 according to one embodiment of the present invention and in accordance with the delivery techniques described with respect to FIGS. 4–8 above. The endoscope 124 described above is first inserted into the proximal end of the delivery device 100. The delivery system is pushed through the urethra until the stent is located in the prostatic urethra 3. Visualization using the endoscope through the lumen of the inner catheter 14 is performed so that correct initial placement may be verified visually. Once it is verified that the distal end of the stent 10 is located at the bladder neck, the locking pin 110 is removed to allow movement of the sheath 16.

In one embodiment, prior to positioning the stent 10 at the bladder neck, a room temperature irrigation solution can be connected to port 118. Preferably, water or saline can be used, which can be hung on an IV pole for gravity infusion. After removal of the locking pin 110, the room temperature irrigation solution is disconnected, and a warm irrigation solution is connected to the port 118. In one embodiment, the temperature of the solution is about 40° C., and can be pre-warmed in a warmer bottle within the operating room.

As shown in FIG. 16, pulling proximally on trigger 114 or trigger 112, the sheath 16 moves proximally relative to the inner and outer tubes 14 and 15 and relative to the stent 10 until the trigger 112 reaches its proximalmost position. At this point the sheath 16 partially exposes the stent 10, and in one embodiment, the stent is about halfway exposed. The trigger 112 can then be removed from the main body 102, as described above.

After reconfirming the stent position at the bladder neck, the rip cord 120 is pulled at least partially to pull the rotator belt up and out of the main body. The middle of the stent will thermally expand, with the distal end of the stent held in by pullwire 25, described above, and the proximal end of the stent being restrained by the sheath 16 and pullwire 32. As described above, pulling on the rip cord rotates outer tube 15 relative to inner tube 14 to expand the stent 10.

With the trigger 112 removed from the main body 102, the trigger 114 is pulled further proximally, as shown in FIG. 17, to fully expose the stent 10 from the sheath 16. As described above, proximal the motion of the trigger 114 also removes the pullwires 25 and 32 from the stent 10 to allow it deploy. The delivery device 100 is then slowly removed with care to avoid inadvertent migration of the stent. During device removal, the operator ensures that no coils of the stent extend beyond the external sphincter. If so, the operator can gently push the stent tip back into the prostatic fossa with grasping forceps.

Thus, while the preferred embodiments of the devices and methods have been described in reference to the environment in which they were developed, they are merely illustrative of the principles of the inventions. Other embodiments and configurations may be devised without departing from the spirit of the inventions and the scope of the appended claims.

What is claimed is:

1. A stent delivery device for delivering a stent into the urethra of a patient, the stent having a first end and a second end, the delivery device comprising:

an inner tube having a distal end releasably connectable to the first end of the stent; and an outer tube being rotatably slideable over the inner tube and having a distal end releasably connectable to the second end of the stent.

2. The stent delivery device of claim 1, further comprising a main body having a proximal end and a distal end, the inner tube and the outer tube extending distally from the main body.

3. The stent delivery device of claim 1, further comprising a sheath being slideable over the outer tube.

4. The stent delivery device of claim 3, further comprising a trigger operably connected to the sheath for moving the sheath along the outer tube.

5. The stent delivery device of claim 3, wherein the sheath is moveable to a first fixed position wherein a distal end of the sheath is between the first and second ends of the stent, and a second position wherein the distal end of the sheath is proximal to the stent.

6. The stent delivery device of claim 1, further comprising a belt operably connected to the outer tube for rotating the outer tube relative to the inner tube.

7. The stent delivery device of claim 2, further comprising a handle extending from the main body.

8. The stent delivery device of claim 1, wherein the stent is releasably connectable to the first and second ends of the stent using at least one pullwire.

9. A method of delivering a stent into a the urethra of a patient, comprising:

providing a stent having a first end and a second end, the first end being releasably attached to an inner tube and the second end being releasably attached to an outer tube which is rotatably slidable over the inner tube;

advancing the stent into the urethra;

rotating the outer tube relative to the inner tube to at least partially expand the stent;

releasing the stent from the inner tube; and releasing the stent from the outer tube.

10. The method of claim 9, wherein the stent is at least partially covered by a sheath prior to advancing the stent into the urethra.

11. The method of claim 10, further comprising sliding the sheath proximally prior to rotating the outer tube relative to the inner tube in order to at least partially expose the stent.

12. The method of claim 11, comprising sliding the sheath proximally such that a distal end of the sheath is located between the proximal and distal ends of the stent.

13. The method of claim 9, wherein the outer tube is rotated relative to the inner tube by pulling a belt attached to the outer tube.

14. The method of claim 12, further comprising sliding the sheath proximally such that the distal end of the sheath is located proximal to the proximal end of the stent after the outer tube is rotated relative to the inner tube.

15. The method of claim 9, wherein the stent is released from the outer tube prior to being released from the inner tube.

16. The method of claim 9, wherein the stent is released from the inner tube prior to being released from the outer tube.

17. The method of claim 9, wherein the stent is released from the inner tube and outer tube simultaneously.

18. The method of claim 9, wherein the stent is releasably attached to the inner and outer tubes using at least one pullwire connecting the ends of the stent to the tubes.

19. The method of claim 18, wherein the stent is released from the tubes by pulling the wire proximally.

20. The method of claim 9, wherein the stent is helical.

21. A stent delivery device for delivering a stent into a lumen of the body, the stent having a first end and a second end, the delivery device comprising:

a main body having a proximal end and a distal end;

an inner tube extending distally from the main body, the inner tube having a distal end releasably connectable to the first end of the stent;

an outer tube extending distally from the main body, the outer tube being rotatably slideable over the inner tube and having a distal end releasably connectable to the second end of the stent;

a sheath extending distally from the main body, the sheath being slideable over the outer tube to at least partially expose the stent; and a belt extending from the main body and attached to the outer tube, wherein pulling of the belt rotates the outer tube relative to the inner tube.

22. The stent delivery device of claim 21, further comprising a handle depending from the main body.

23. The stent delivery device of claim 21, further comprising a trigger depending from the main body and being slideable in relation thereto, the trigger being operably connected to the sheath to move the sheath.

24. The stent delivery device of claim 21, further comprising a stop in the main body that limits the proximal movement of the sheath.

25. The stent delivery device of claim 24, wherein the stop includes a removable trigger.

26. The stent delivery device of claim 21, further comprising a pull wire for releasably connecting the inner tube to the first end of the stent.

27. The stent delivery device of claim 21, further comprising a pull wire for releasably connecting the outer tube to the second end of the stent.

28. A stent deployment device, comprising:

a tubular body, having a proximal end and a distal end, the tubular body comprising a first and a second stent support;

a hand piece on the proximal end of the tubular body;

a first control on the hand piece, for manipulating the first stent support; and a second control on the hand piece, for manipulating the second stent support.

29. A stent deployment device as in claim 28, wherein the first stent support comprises an outer tubular sleeve for surrounding the stent.

30. A stent deployment device as in claim 29, wherein the first control comprises a control for proximally retracting the first stent support to expose at least a portion of the stent.

31. A stent deployment device as in claim 28, wherein the second stent support comprises a tubular body which is releasably connected to at least a first end of the stent.

32. A stent deployment device as in claim 31, wherein the second control comprises a control for rotating the second stent support.

33. A stent deployment device as in claim 30, wherein the first control comprises a releasable stop to stop proximal retraction of the first stent support at a point wheel the stent is only partially exposed.

34. A stent deployment device as in claim 30, wherein the first control comprises an axially movable lever.

35. A stent deployment device as in claim 32, wherein the second control comprises a belt which is wrapped around the second stent support.

36. A stent deployment device as in claim 28, further comprising a first pull wire, for releasably securing the stent to the second stent support.

37. A stent deployment device as in claim 28, further comprising a third stent support, releasably connected to at least a second end of the stent.

38. A stent deployment device as in claim 37, further comprising a second pull wire, for releasably securing the stent to the third stent support.

39. A stent deployment device as in claim 38, wherein the third stent support comprises an inner tube and the second stent support comprises an intermediate tube, concentrically carried by the inner tube.

40. A stent deployment device as in claim 39, wherein the first stent support comprises an outer tube, concentrically carried by the intermediate tube.

\* \* \* \* \*